(12) United States Patent
Al-Turaikl

(10) Patent No.: US 7,416,565 B1
(45) Date of Patent: Aug. 26, 2008

(54) ADJUSTABLE TENSION PROSTHETIC ANKLE ROTATORY DEVICE FOR LOWER LIMB APPARATUS

(76) Inventor: Mohmmed H. S. Al-Turaikl, P.O. Box 91409, Riyadh (SA) 11633

( * ) Notice: Subject to any disclaimer, the term of this patent is extended or adjusted under 35 U.S.C. 154(b) by 0 days.

(21) Appl. No.: 11/931,958

(22) Filed: Oct. 31, 2007

Related U.S. Application Data

(60) Provisional application No. 60/949,063, filed on Jul. 11, 2007.

(51) Int. Cl.
*A61F 2/66* (2006.01)
*A61F 2/68* (2006.01)
(52) U.S. Cl. .......................................... 623/52
(58) Field of Classification Search ............ 623/47–56, 623/38
See application file for complete search history.

(56) References Cited

U.S. PATENT DOCUMENTS

| | | | |
|---|---|---|---|
| 4,865,611 A | 9/1989 | Al-Turaiki | |
| 4,988,361 A | 1/1991 | Cooper | |
| 5,156,630 A | 10/1992 | Rappoport et al. | |
| 5,728,175 A * | 3/1998 | Rincoe | ..................... 623/49 |

* cited by examiner

*Primary Examiner*—Bruce Snow
(74) *Attorney, Agent, or Firm*—Groover & Associates

(57) ABSTRACT

A transtibial patellar tendon bearing (PTB) prosthesis for below the knee amputees is disclosed. The prosthesis includes a socket, and a foot prosthesis attached to a modular shank component using a foot rotator device. Using the rotator device, the foot component of the prosthesis may be smoothly and axially rotated internally or externally ±150° with respect to the shank component about the axis of the shank component. The wide range of axial rotation enables a more even load distribution on the whole lower limb of an amputee and enables an amputee to comfortably assume a wide range of biomechanical positions, such as sitting or kneeling. A recoil spring, having a selectable tension, is positioned within the rotatable component and selectively limits and retains the relative rotation of the upper portion and the lower portions. A locking mechanism selectively prevents rotation when the foot component is engaged.

18 Claims, 3 Drawing Sheets

ADJUSTABLE TENSION PROSTHETIC ANKLE ROTATORY DEVICE FOR LOWER LIMB APPARATUS

CROSS-REFERENCE TO RELATED APPLICATIONS

This application claims the benefit of Provisional Patent Application Ser. No. 60/949,063, filed on Jul. 11, 2007 entitled Adjustable Tension Prosthetic Ankle Rotatory Device for Lower Limb Amputees, and incorporated by reference for all purposes herein.

BACKGROUND OF THE INVENTION

The disclosure relates to modular prosthesis assemblies, and more specifically, to prosthesis assemblies for transtibial, or below the knee, amputees.

Prosthetic assemblies for transtibial amputees may limit or constrain the flexibility or range of lower body movement particularly during difficult biomechanical positions including, but not limited to, kneeling, squatting, sitting, i.e. kneeling while sitting back on the heels, and the transitions between such positions.

These biomechanical positions may cause discomfort to an amputee or may induce pain or strains in the knees, hip and/or back. In the prior art, various prosthetic assemblies exist but very few specifically address the range of motion and position difficulties experienced by transtibial amputees that assume the positions of kneeling, squatting, sitting, or transitioning between these positions.

For example, U.S. Pat. No. 7,052,519 to Gramnäs entitled Prosthetic Leg and Foot Apparatus discloses an arrangement for a leg prosthesis provided with a foot which is connected to the leg prosthesis via an articulated axle. However, Gramnäs does not address the positional problems experienced by transtibial amputees.

U.S. Pat. No. 4,038,705 to Owens et al. entitled Rotational Joint Assembly For the Prosthetic Leg discloses a rotational joint assembly for a prosthetic leg which enables an artificial foot to rotate slightly which a person is walking, running, or turning. However, Owens et al. does not disclose a solution to the physical position problem experienced by transtibial amputees.

U.S. Pat. No. 7,112,227 to Doddroe et al., entitled Multi-axis Prosthetic Ankle Joint discloses a multi-axis prosthetic ankle for connection of a prosthetic lower leg to a prosthetic foot. However, Doddroe et al. does not disclose a solution to the physical position problems experienced by transtibial amputees.

U.S. Pat. No. 6,187,052 to Molino et al. entitled Prosthetic Ankle Joint discloses a prosthetic ankle joint that mimics natural ankle motion but does not specifically address the positional position problems experienced by transtibial amputees.

WO2005/037151 discloses an artificial multi-axes knee joint which does not address the positional problems experienced by transtibial amputees.

However, U.S. Pat. No. 4,865,611 issued to Al-Turaiki entitled Lockable Rotating Ankle Joint for Modular Below-Knee Prosthesis addresses the flexibility for the difficult biomechanical positions for a transtibial amputee. Al-Turaiki discloses a patellar tendon bearing (PTB) prosthesis that has a socket, a modular shank component, and a foot component which is rotatably attached to the shank component. The rotatable foot attachment allows the foot component to be axially rotated inwardly or outwardly at ±90° angles with respect to the shank component of the prosthesis.

SUMMARY OF THE INVENTION

Increasing the axial foot rotation relative to the shank piece in a modular lower limb, endoskeletal system, prosthesis facilitates more comfortable biomechanical positions such as kneeling, squatting, sitting, i.e. kneeling while sitting back on the heels and transitions between such positions. The disclosed rotatable standard patellar tendon bearing (PTB) prosthesis helps to alleviate the discomfort experienced by amputees assuming many common biomechanical positions.

Further, enabling the foot component of a prosthesis to axially rotate internally or externally with respect to the shank component of the prosthesis promotes a more even distribution of body weight on the whole lower limb during a sitting, kneeling or other various positions assumed by an amputee.

An advantage offered by this arrangement is that use of the device enables Muslims, particularly those with below knee amputations, to carry out their religious duties with minimal inconvenience. The assembly offers an immediate, safe and low cost solution to these existing problems.

Additionally, the disclosed design includes a built-in universal tube clamp interface as a standard foot component of the prosthesis. Therefore the foot component may be incorporated into any type of conventional PTB prosthesis or shank prosthesis without modification of the rotary mechanism of the foot component.

Further, the foot rotator assembly may be adjusted using tension controlled springs adjusted for the weight and activity level of an amputee.

BRIEF DESCRIPTION OF THE DRAWINGS

The disclosed inventions will be described with reference to the accompanying drawings, which show important sample embodiments of the invention and which are incorporated in the specification hereof by reference, wherein.

DESCRIPTION OF THE PREFERRED EMBODIMENTS

The present application discloses embodiments of an Adjustable Tension Prosthetic Ankle Rotatory Device for Lower-Limb Amputees. Details are set forth to provide a thorough understanding of the embodiments of the present inventions with the help of the drawings but not limited to.

The features, structures, materials, and characteristics of the inventions can be combined in any suitable manner in one or more embodiments.

Figure 1:
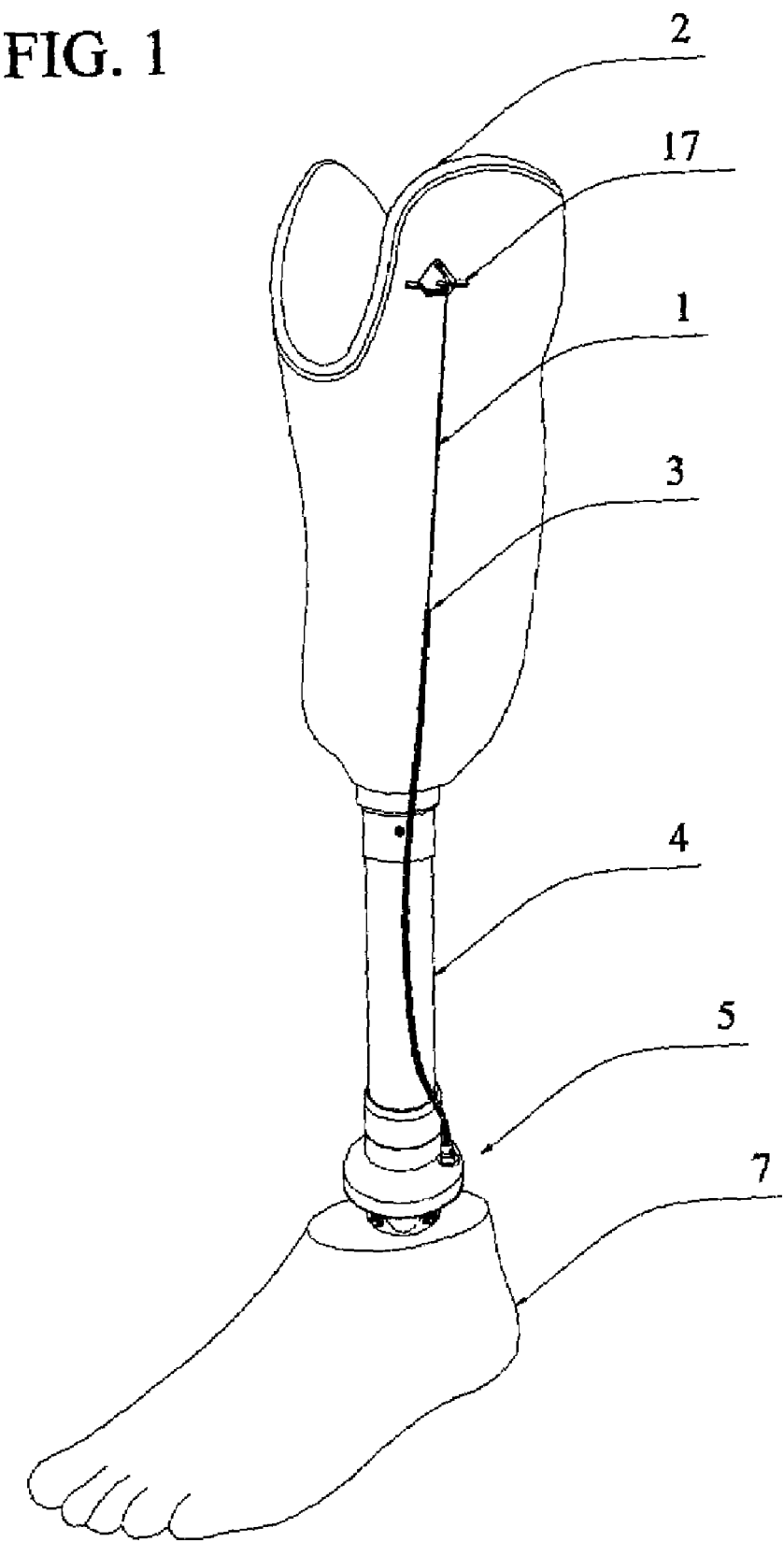
FIG. 1 is a side perspective view of the below knee prosthesis assembly according to one embodiment of the disclosure.

FIG. 1 illustrates a below knee prosthesis according to one embodiment. A modular patellar tendon bearing prosthesis may include an appendage socket 2 that securely accommodates the stump of an amputated leg. The appendage socket 2 is physically connected to a modular shank component 4, for example, a modular below-knee prosthesis. The modular shank component 4 is rotatably attached to a modular foot component 7, for example, a modular foot prosthesis.

The modular foot component 7 may be rotatably attached to the modular shank component 4 with a foot rotator assembly 5. Foot rotator assembly 5 may be designed to allow about one-hundred fifty degrees of internal and external lateral rotation (±150°). The precise angle of rotation may be manually selected by a user or determined by the weight of the user as pressure is applied to the tension-adjusted foot rotator assembly 5. The foot rotator assembly 5 may include integrated universal clamp adapter 20 and universal tube clamp interface 26 in FIGS. 2 and 3 to secure the connection of the foot rotator assembly 5 to the modular foot component 7 and the modular shank component 4.

The rotation of the modular foot component 7 may be controlled by a locking mechanism integrated within the foot rotator assembly 5. The integrated locking mechanism may be used to prevent rotation of the modular foot component 7 relative to the modular shank component 4 from taking place during movement, such as walking or running.

The integrated locking mechanism may be activated by manual operation of a control handle 17. The control handle 17 may be connected to a cable 1 that is surrounded by cable sheath 3 and extends to the foot rotator assembly. The cable 1 is secured to the integrated locking mechanism.

Positioning of the modular foot component 7 may be achieved by manually pulling up on control handle 17 while pressing the modular foot component 7 against the ground allowing a desired axial rotation of about ±150° of the modular foot component 7 about the medial/lateral axis, with respect to the modular shank component 4, and a selected axial torque.

The control handle 17 may be pulled by a user anytime a positional adjustment of the modular foot component 7 may be required. For example, during prolonged kneeling or sitting, a positional adjustment may be needed to promote a more even distribution of body weight on the whole lower limb including the modular shank component 4 and the stump. Pulling the control handle 17 disengages the locking mechanism and enables an axial rotation of the modular foot component.

Figure 2:
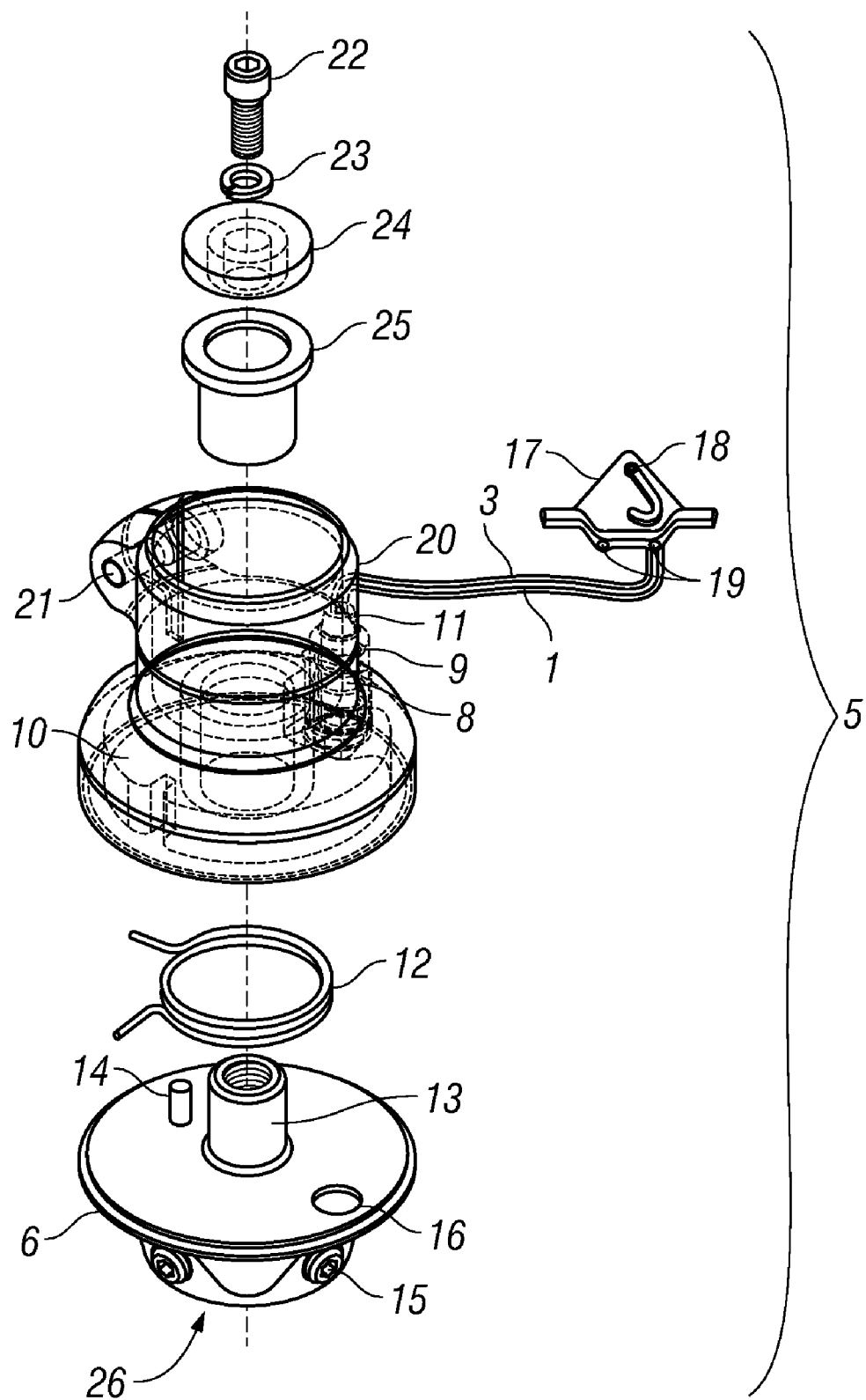
FIG. 2 illustrates an exploded three-dimensional view of a rotatable connector according to an embodiment of the disclosure.

FIG. 2 is an exploded view details the components of the foot rotator assembly 5. The foot rotator assembly 5 comprises an upper module 10 that fits together with a lower annular receptor module 6. The upper module 10 of the foot rotator assembly 5 may be fastened to the modular shank component 4 with an integrated clamp adapter 20 and locking screw 21. The lower annular receptor module 6 of the foot rotator assembly 5 may be fastened to the modular foot component 7 with an integrated tube clamp interface 26 and set screws 15. The integrated clamp adapter 20 with locking screw 21 and integrated tube clamp interface 26 and set screws 15 enable easy adaptability and incorporation of the rotator device onto any conventional shank prosthesis. The foot rotator assembly 5 may be implemented to provide low friction rotation and noise reduction. Low friction rotation and noise reduction may preferably be achieved through the use of CAD-CAM designed bush fitting systems to increase the durability and provide decreased friction.

The upper module 10 of the foot rotator assembly 5 may include a bushing 25, and preferably a frictionless brass bushing. The brass bushing 25 may be held in place using a bolt 22, a spacer washer 24 and a spring washer 23. The bushing 25 may slide into and engage a tension controlled recoil spring 12.

The upper module 10 also uses the integrated locking mechanism that may be comprised of an axially sliding locking pin 11 that is positioned within a loaded locking spring 9 and housing 8. The integrated locking mechanism may be preferably implemented by a single point auto-locking system to reduce misalignment and increase stability. However, other locking mechanisms, such as, multi-point locking systems, or other systems that would readily suggest themselves to one of ordinary skill in the art may be used.

A lower annular receptor module 6 may be provided with a latch hole 16 to receive the locking pin 11 as it is rotated through various positions. One or more latch holes may be provided depending on the locking system utilized. Locking pin 11 may be engaged and disengaged from latch hole 16 by activation of the attached cable 1. A spring guide pin 14 and a latch hole 16 are provided in the upper surface of the lower annular receptor module 6. When locking pin 11 is engaged, locking spring 9 may provide sufficient spring tension to hold the locking pin 11 in latch hole 16.

The cable 1 may be surrounded by cable sheath 3 and configured to attach to the control handle 17. The cable sheath 3 may be slidable or may adhere to the cable. The length of the cable 1 may be adjusted using set screws 19. Other fastening means may be used that would readily suggest themselves to one of ordinary skill in the art. The cable 1 may be vertically affixed to the surface of the appendage socket 2 through the control handle 17 attachment screw 18. The cable sheath 3 may extend the entire length of the cable 1 or may only cover a portion of the cable 1.

The degree of ease with which the foot component 7 may be adjusted is determined by selection of an appropriate tension-controlled recoil spring 12. The recoil spring 12 may be selected to provide a singular discrete tension. The recoil spring 12 is inserted to the upper module housing 10 and is engaged with spring guider pin 14 and the threaded collar on lower module 13.

Figure 3:
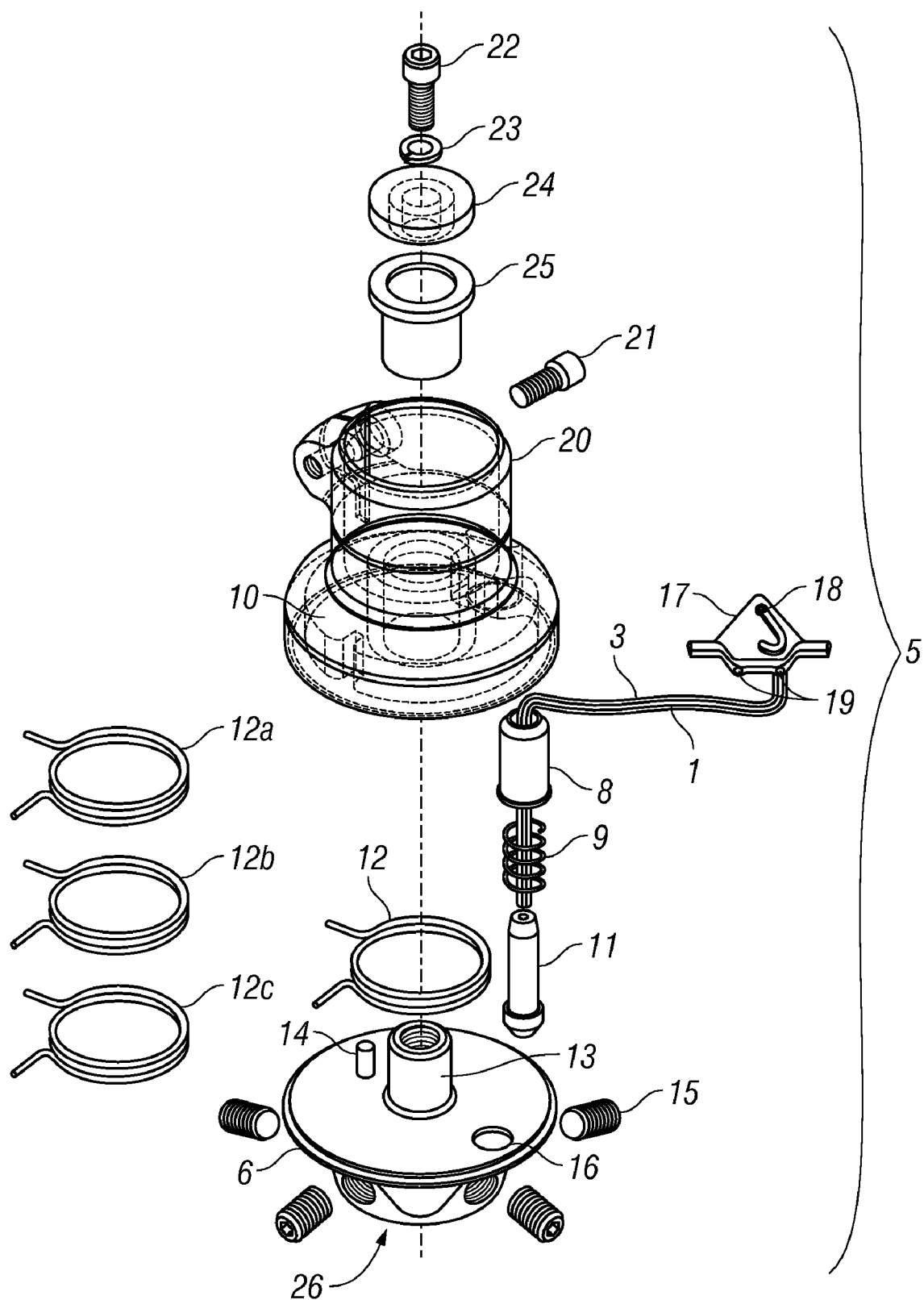
FIG. 3 illustrates a more detailed exploded three-dimensional view of the rotatable connector illustrated in FIG. 2.

FIG. 3 depicts another exploded view of the foot rotator assembly 5 in accordance with one embodiment. In FIG. 3, three springs having exemplary differentiated tensions 12a, 12b, 12c are shown. Preselection of adjustable spring tensions allow torque adjustment according to body weight and activity level.

Preselecting a recoil spring 12 with a specific tension form e.g. 12a, 12b, 12c, also promotes auto-retention of a particular biomechanical position, and ease of rebound from one position to a previous or another position or ease of movement within positions.

One example of the auto-retention capability could be illustrating by an ease of rebound movement within a double support position. A double support position refers to the biomechanical stance assumed when both feet are in contact with the ground. Within a double support position, there could be a series of motions involving, for example, a squat-stand-squat, (i.e. a squatting to standing to squatting) position. Starting from the squatting position, the recoil spring 12 would retain the configuration of the squat position as a transition is made to a standing position. A subsequent transition from the stand position to the squat position could then easily be resumed because the recoil spring would already have retained the squat position configuration allowing an easy assumption of and rebound to the squat position. This squat-stand-squat example of the recoil spring must be treated as merely exemplary and is not representative of the numerous various biomechanical transitions or rebound positions that would be obvious to one of ordinary skill in the art.

The locking pin 11 when engaged in latch hole 16 fixes the modular foot component 7 to the lower annular receptor module 6 and prevents rotation of the modular foot component 7 during walking or running. The locking pin 11 is part of the spring loaded locking mechanism. The spring loaded locking mechanism may includes housing 8 that encloses or surrounds the locking spring 9, and the locking pin 11, a cable 1 that is enclosed by cable sheath 3 and extends and connects to control handle 17 at one end and to the locking pin 11 at another end. The cable 1 connected to the locking pin 11 may be used to manually urge the locking pin 11 away from latch hole 16 against the force of the loaded locking spring 9.

The universal tube clamp interface 26 of the lower annular receptor module 6 may be fastened securely to any modular foot component 7 prosthesis by tightening a plurality of set screws 15 that are integrated into the universal tube clamp interface 26.

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

MODIFICATIONS AND VARIATIONS

As will be recognized by those skilled in the art, the innovative concepts described in the present application can be modified and varied over a tremendous range of applications, and accordingly the scope of patented subject matter is not limited by any of the specific exemplary teachings given.

In one embodiment, a below-knee patellar tendon bearing prosthesis is disclosed. The prosthesis comprises a modular socket physically attachable to the stump of an amputated leg, a modular shank member physically connected to the modular socket, a modular foot component, and a rotatable assembly connected to and allowing lateral rotation between the foot component and modular shank members, over at least about +150 degrees internally and externally.

The rotator assembly has upper and lower modules and includes a locking mechanism selectively preventing rotation when engaged, wherein the locking mechanism includes an axially slidable locking pin carried by the upper module, a latch hole formed in the lower module and receiving the locking pin in acquired rotational positions of the lower portion, a locking spring positioned to provide tension to the locking pin toward the latch hole, a cable connected to the locking pin for manually urging the locking pin away from the latch hole against the force of the locking spring, and a cable sheath carried by a portion of the prosthesis above the rotator assembly to slidably retain the locking cable.

In another embodiment, a selectable tension prosthesis assembly is disclosed. The assembly includes an appendage socket attachable to a user, a modular shank component connected to the appendage socket, a modular foot prosthesis, and a rotatable assembly connected to the modular foot prosthesis and the modular shank component and allowing rotation of the prosthesis relative to the shank component about the axis of the shank internally and externally about ±150 degrees, wherein the rotatable assembly includes an upper portion fixedly connected to the shank. A lower portion is fixedly connected to the prosthesis and a selectable tension-controlled recoil spring is positioned within the rotatable assembly, and is connected to selectively limit and retain the relative rotation of the upper portion and the lower portion.

In another embodiment, a leg prosthesis assembly comprises a modular shank member, a modular prosthetic foot component connected to the shank member, a rotatable assembly connected between said prosthetic foot component and said shank member, and a locking mechanism selectively preventing rotation of said rotatable assembly when engaged.

In another embodiment, a leg prosthesis assembly is disclosed including a lower leg replacement member, and a modular prosthetic foot component, attached to said lower leg replacement member, with an anti-rotation lock which is unlocked by the user when rotation of the foot component around the axis of the replacement member is needed.

In another embodiment, a method of using an artificial limb is disclosed. The method includes manually preventing rotation of a foot prosthesis around the axis of a below-knee prosthesis; and manually enabling said rotation of said foot prosthesis for prolonged kneeling.

The present application, as disclosed, should not be construed as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 U.S.C. § 112 unless the exact words "means for" are followed by a participle.

The claims as filed are intended to be as comprehensive as possible, and NO subject matter is intentionally relinquished, dedicated, or abandoned.

What is claimed is:

1. A leg prosthesis assembly, comprising:
    a modular shank member;
    a modular prosthetic foot component rotatably connected to said shank member, to allow rotation about the axial axis of said shank member;
    a rotatable assembly, connected between said modular prosthetic foot component and said shank member, and allowing internal and external lateral of about ±150 degrees rotation, the rotatable assembly including a selectable tension-controlled recoil spring positioned within the rotatable assembly, the rotatable assembly comprising an upper module and a lower module, the upper module including the selectable tension-controlled recoil spring that promotes auto-retention of a particular biomechanical position; and
    a locking mechanism selectively preventing rotation of said rotatable assembly when engaged.

2. The leg prosthesis assembly of claim 1, further comprising:
    an appendage socket physically attachable to the stump of an amputated leg at one end and physically connected to the modular shank member at another end.

3. The leg prosthesis assembly of claim 1, wherein the rotatable assembly includes a frictionless brass bushing that is engaged within said recoil spring and provides low friction rotation and noise reduction.

4. The leg prosthesis assembly of claim 1, wherein the modular prosthetic foot component is secured to the lower module of the rotatable assembly by means of a universal clamp interface.

5. The leg prosthesis assembly of claim 1, wherein the locking mechanism includes a locking pin, a locking spring, a housing component that surrounds the locking pin and locking spring, a cable attached at one end to the locking pin and at another end to a control handle, and a latch hole that receives said locking pin.

6. The leg prosthesis assembly of claim 1, wherein the locking mechanism is integrated within the rotatable assembly.

7. The leg prosthesis assembly of claim 1, wherein a selected axial rotation of the prosthetic foot component is controlled by operating the locking mechanism.

8. The leg prosthesis assembly of claim 1, wherein the locking mechanism is a single-point locking mechanism.

9. A selectable tension prosthesis assembly, comprising:
an appendage socket attachable to a user;
a modular shank component connected to the appendage socket;
a modular foot prosthesis; and
a rotatable assembly connected to the modular foot prosthesis and the modular shank component and allowing rotation of the modular foot prosthesis relative to the shank component about the axis of the shank internally and externally about +150 degrees;
wherein the rotatable assembly includes:
an upper portion fixedly connected to the shank;
a lower portion fixedly connected to the prosthesis, and
a selectable tension-controlled recoil spring positioned within the rotatable assembly connected to selectively limit and retain the relative rotation of the upper portion and the lower portion.

10. The selectable tension prosthesis assembly of claim 9, wherein the rotatable assembly includes a locking mechanism that selectively prevents axial rotation of the prosthesis relative to the shank component.

11. The selectable tension prosthesis assembly of claim 10, wherein the locking mechanism includes a locking pin, a locking spring, a housing component that surrounds the locking pin and locking spring, a cable attached at one end to the locking pin and at another end to a control handle, and a latch hole that receives said locking pin.

12. The selectable tension prosthesis assembly of claim 9, wherein the rotatable assembly includes a frictionless brass bushing that is engaged within a recoil spring and provides low friction rotation and noise reduction.

13. A below-knee patellar tendon bearing prosthesis assembly, comprising:
a modular socket physically attachable to the stump of an amputated;
a modular shank member physically connected to said modular socket;
a modular foot component; and
a rotator assembly connected to and allowing lateral rotation between said modular foot component and said modular shank member, about the axis of said shank member, over at least about ±150 degrees internally and externally;
said rotator assembly having upper and lower modules and including:
a locking mechanism selectively preventing rotation when engaged, wherein the locking mechanism includes an axially slidable locking pin;
a latch hole formed in the lower module and receiving the locking pin in acquired rotational positions of the lower module;
a locking spring positioned to provide tension to the locking pin toward the latch hole;
a cable connected to the locking pin for manually urging the locking pin away from the latch hole against the force of the locking spring;
a cable sheath carried by a portion of the prosthesis above the rotator assembly to slidably retain the cable; and
a recoil spring, having a selectable tension and positioned within the upper module of said rotator assembly, that selectively limits and retains the relative rotation of the upper module and lower module.

14. The prosthesis assembly of claim 13, wherein said upper module of said rotator assembly is fixedly connected to said modular shank member, and said lower module is fixedly connected to said modular foot component.

15. The prosthesis assembly of claim 13, wherein the modular foot component is secured to the lower module of the rotator assembly by means of a universal tube clamp interface.

16. The prosthesis assembly of claim 13, wherein the modular shank component is fastened to said rotator assembly by means of an integrated clamp adapter.

17. The prosthesis assembly of claim 13, wherein the locking mechanism is a single-point locking mechanism.

18. The prosthesis assembly of claim 13, wherein the locking mechanism is a multi-point locking system.

* * * * *